United States Patent [19]

Lazzara et al.

[11] Patent Number: 4,846,683
[45] Date of Patent: Jul. 11, 1989

[54] AXIALLY SHORT DENTAL IMPLANT FIXTURE

[75] Inventors: Richard J. Lazzara, Lake Worth; Keith D. Beaty, West Palm Beach, both of Fla.

[73] Assignee: Implant Innovations, Inc., W. Palm Beach, Fla.

[21] Appl. No.: 210,331

[22] Filed: Jun. 23, 1988

[51] Int. Cl.⁴ .................................................. A61C 8/00
[52] U.S. Cl. ........................................ 433/173; 433/174
[58] Field of Search ................ 433/173, 174, 175, 176

[56] References Cited

U.S. PATENT DOCUMENTS

| | | | |
|---|---|---|---|
| 4,552,532 | 11/1985 | Mozsary | 433/174 |
| 4,575,340 | 3/1986 | Lustig | 433/173 |
| 4,713,003 | 12/1987 | Symington et al. | 433/173 |
| 4,713,004 | 12/1987 | Linkow et al. | 433/174 |

Primary Examiner—John J. Wilson
Attorney, Agent, or Firm—Alfred H. Rosen

[57] ABSTRACT

A dental implant fixture for use in a shallow bore in a jawbone has a flange around its gingival end which overlies the jawbone around the bore when the fixture is installed in the bore. The bore is countersunk to receive the flange, preferably deeper than the thickness of the flange to encourage growth of bone over the flange. Pressure on the fixture is taken up by the flange.

8 Claims, 1 Drawing Sheet

AXIALLY SHORT DENTAL IMPLANT FIXTURE

BACKGROUND OF THE INVENTION

This invention relates to dental implant systems, in particular to systems wherein a cylindrically shaped implant fixture is implanted into a bore prepared to receive it in the jawbone of a patient.

In a typical dental implant system the fixture is press-fitted or screwed into the receiving bore to a depth ranging from about 7 mm. to about 18 mm. In molar regions near the sinus cavities and the mandibular canal depths in this range are not available. Risk of invading the sinus cavities and the mandibular canal is generally avoided, the result being that in these posterior regions only about 4 or 5 mm. of bone depth is available in which to prepare a bore to receive a dental implant. In the present state of the art of dental implantology bore depths less than 7 mm. are not considered useful. Osseointegration required to fix an implant fixture in the jawbone in a bore of shallow depth less than about 7 mm., is difficult to achieve. The greater the surface area in contact with bone, the better is the prognosis.

GENERAL NATURE OF THE INVENTION

In accordance with the present invention a dental implant fixture having a cylindrically-shaped post portion which may be as little as 4 mm. long has an annular flange extending laterally around its gingival end for overlying the surface of the jawbone around the receiving bore when the fixture is implanted in it. When, after osseointegration has taken place, a prosthesis is fitted to the implant fixture, the compression forces of mastication may be taken up at least in part by the flange, which also provides increased surface area for osseointegration. The combination of such flanged dental implant fixture and an intermediate component joined to it, on or with the aid of which a prosthodontic restoration can be fashioned, provides support for such restorations in molar regions of a patient's jaws where up to now it has been deemed unwise to attempt them.

A flanged implant fixture according to the invention presents a support surface which has a greater diameter than the prior-available implant fixtures, for which a large number of intermediate components have already been provided having diameter dimensions selected to mate with them. The flanged implant fixtures of the invention are adaptable for use in combination with existing intermediate components while providing increased surface area for osseointegration, as well as with new components designed to take particular advantage of the larger bearing-surface diameter of the new flanged implant fixtures. To this end, a new trans-tissue component is provided for mating with known supragingival components while transmitting compression forces, in use, directly to the bearing surface of the flange.

BRIEF DESCRIPTION OF THE DRAWINGS

The invention is further explained with the aid of the description of exemplary embodiments of it that follows, referring to the accompanying drawings, in which.

DETAILED DESCRIPTION OF THE DRAWINGS

Figure 1:
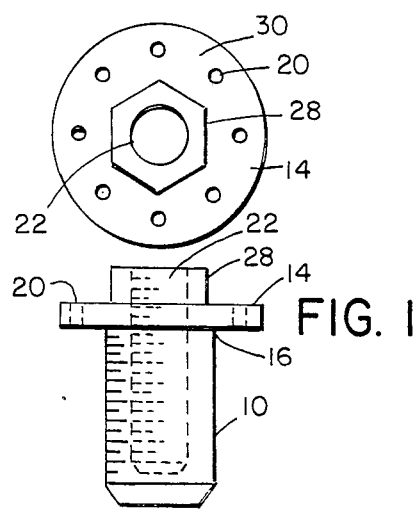
FIG. 1 is side and plan views of an implant fixture.
Figure 2:
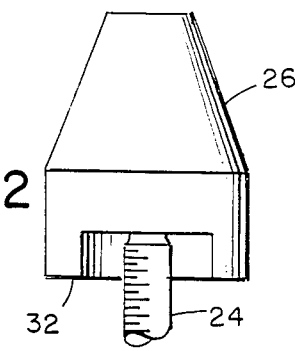
FIG. 2 is a side view of an intermediate component.
Figure 3:
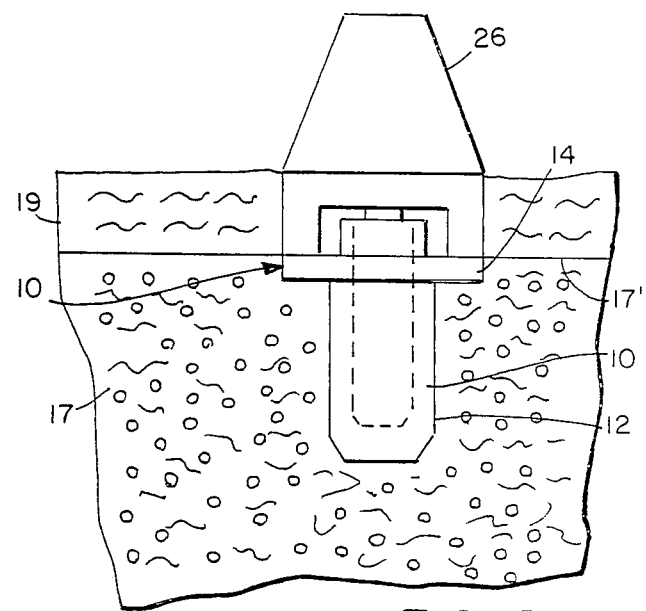
FIG. 3 shows the combination of a fixture of FIG. 1 and a component of FIG. 2 fixed in a section of jawbone.

The dental implant fixture shown in FIG. 1 has a cylindrical implant body 10 which may be externally threaded, as shown; alternatively the implant body may be a smooth cylinder intended to be press-fitted in the bore 12 prepared to receive it, as appears in FIG. 3. An annular flange 14 is fixed to the gingival end 16 of the implant body. The bone 17 is recessed around the bore 12 to receive the flange when the implant body 10 is installed in the bore, the recess 18 having diameter and depth corresponding respectively to the diameter and thickness of the flange. Holes 20 are provided through the flange to allow interlocking growth of bone with the flange, so as to increase the area over which osseointegration takes place. An internally threaded receiving bore 22 is engagement means for mating with the threaded post 24 of a prosthodontic restoration component 26, shown in FIG. 2. A boss 28 extending supragingivally from the flange 14 surrounds the opening into the receiving bore; this boss may have a non-circular, e.g; hexagonal, cross-sectional shape, as shown, for anti-rotational attachment of components, if that feature is desired.

The bottom annular surface 32 of the component 26 meets the top surface 30 of the flange when the component 26 is joined to the implant fixture's implant body 10 by screwing the post 24 into the receiving bore 22. When, after a restoration (not shown) has been fashioned on the component 26, the compression forces of mastication during use of the restoration will be imposed on the implant fixture at least in part on the flange 14, rather than entirely on the implant body 10 as would occur in the absence of the flange. This sharing of compression forces between the flange and the implant body makes feasible the use of an implant body that is only 4 or 5 mm. long.

In the implant fixtures presently in use the diameter of the implanted body is in the range of 3 to 4 mm., and the diameter of the implant body 10 may be in the same range, so that use of the flanged implant fixture of the invention will not require a new or different set of surgical implements to prepare the bore 12 in the jawbone 17. However, the flange 14 has a larger diameter, for example, 6 mm, depending on how widely it is desired and feasible in a given case to diffuse the imposed forces of compression. This gives to the restorative dentist a variety of options. On the one hand a component, such as is illustrated in FIG. 2, which has the same diameter as the flange may be used. On the other hand the restorative dentist may prefer to use existing components which are available for use with the longer implant fixtures presently in use and well-known. The embodiment of the invention illustrated in FIGS. 4 and 5 provides this option.

Figure 4:
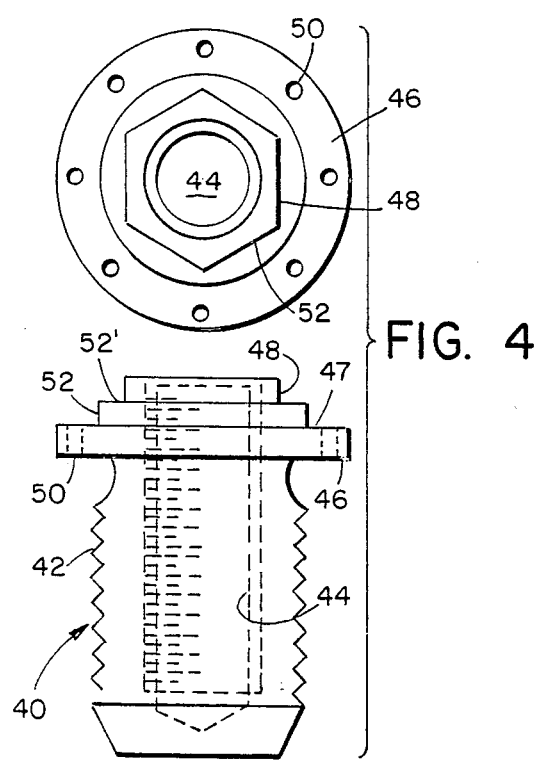
FIG. 4 is side and plan views of another implant fixture.

The implant fixture 40 shown in FIG. 4 has an implant body 42 (here shown, by way of example, as externally threaded), an internally-threaded receiving bore 44, a flange 46 and a non-circular boss 48 surrounding the opening into the receiving bore, corresponding to the implant fixture shown in FIG. 1. In addition the implant fixture 40 has a circular boss 52 on the flange 46, between the flange and the non-circular boss 48, providing an annular bearing surface 52' surrounding the non-circular boss 48 at its base. The diameter of the circular boss 52 is the same as the diameter of the implant body 42. Holes 50 through the flange 46 are provided to encourage osseointegration including interlocking growth of bone.

Figure 5A:
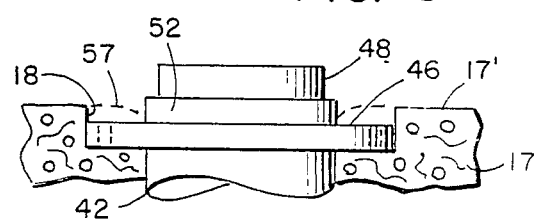
FIG. 5A illustrates a preferred use of the fixture according to FIG. 4 to increase the surface area for osseointegration.
Figure 5:
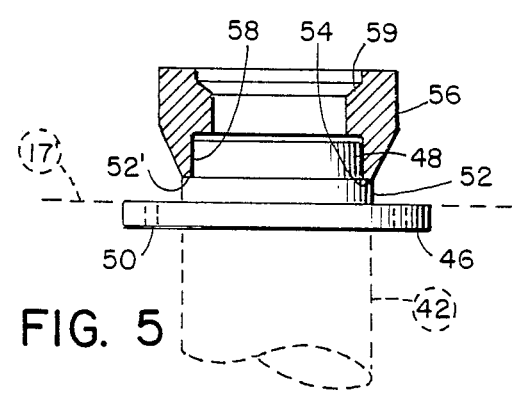
FIG. 5 is a side-section view of an intermediate component of the smaller prior-standard diameter fitted to a fixture according to FIG. 4.

Referring to FIG. 5, a trans-tissue component 56, which may be one of an existing design intended for use with prior-existing longer implant fixtures, has a non-circular socket 58 for non-rotational engagement with the non-circular boss 48, and an annular bearing surface 54 which meets the bearing surface 52' of the implant fixture when the component 56 is attached to the implant fixture 40 in the same way that it would be attached to a prior-existing longer implant fixture lacking the flange 46. A beveled surface 59 provides bearing for the head of a bolt (not shown) to be screwed into the receiving bore 44, to join the component 56 to the implant fixture 40. Forces of compression imposed on the implant fixture 40 during use are transmitted via contact between these bearing surfaces 54 and 52' to the implant body 42 and to the flange 46 which is rigidly attached to it. As is illustrated in FIG. 3 the flange 46 is recessed into the bone 17, so that the top surface of the flange may be flush with the surface 17' of the jawbone. Preferably, the depth of the recess 18 is greater than the thickness of the flange 46 so that the top surface of the flange is below the bone surface 17', as is shown in FIG. 5A, allowing bone to grow over the top surface of the flange, as is indicated at 57. The trans-tissue component will in either case function in substantially the same way it would function if it were installed on an implant fixture lacking the flange 46.

Figure 6:
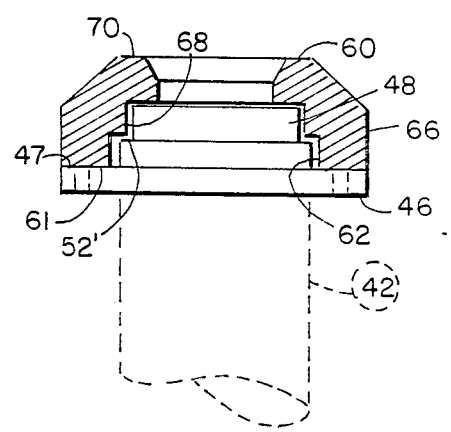
FIG. 6 is a side-sectional view of a new trans-tissue component of the invention fitted to a fixture according to FIG. 4.

The trans-tissue component 66 shown in FIG. 6 is designed to impose forces of compression directly on the top surface 47 of the flange 46. At its lower end this component has a circular recess 62 dimensioned to loosely envelop to circular boss 52 of the implant fixture 40, providing a lower annular bearing surface 64 to mate with the top surface 47 of the flange 46. Immediately above and adjacent the circular recess 62 is a non-circular socket 68, smaller in transverse dimension than the circular recess, and dimensioned for non-rotational engagement with the non-circular boss 48 of the implant fixture. At the top, that is, in the region extending supragingivally from the flange 46, the trans-tissue component 66 tapers to the smaller external diameter of the implant body 42, providing at its supragingival end a top surface 70 which is substantially similar to the annular bearing surface 52' of the implant fixture 40. The axial dimensions of the recess 62 and the socket 68 can be chosen such that no compressive force is applied to the top surface 52' of the circular boss 52, or to the top surface of the non-circular boss 48, so that the entire forces of compression are imposed directly on the top surface 47 of the flange 46 through the bearing surface 64. In that case gaps will be left between the relevant intermediate transverse annular surfaces, as appears in FIG. 6. Alternatively, if closer tolerances are observed, intermediate transverse annular surfaces can also be brought into contact with each other. In either case the forces of compression will be diffused over a wider area by the flange 46.

The trans-tissue components shown in FIGS. 5 and 6 can be affixed to the implant fixture 40 in a known way using a threaded bolt (not shown) engaged in the receiving bore 44. The invention is not to be deemed limited to use with components illustrated. The illustrations are by way of example only. The invention is intended to provide new implant fixtures which will extend the capabilities of prosthodontic restoration.

We claim:

1. In combination, a dental implant fixture having an elongated substantially cylindrical implantation body having a first diameter for implantation in a bore having a similar diameter made in the jawbone of a patient to receive said implant fixture, said implant fixture when so implanted having a gingival end located in the opening into said bore, an annular flange on said body extending therefrom laterally around said gingival end to a second larger diameter for overlying the surface of said jawbone around said opening when said fixture is so implanted, a receiving bore in said implantation body opening centrally through said flange, prosthodontic restoration component means having a bearing surface for contacting said implant fixture at said gingival end, means for engaging in said receiving bore to join said restoration component means to said implant fixture, said implant fixture having an annular boss extending supragingivally from said flange around said receiving bore opening concentric with and having an outer diameter which is the same as said first diameter of said implantation body, said bearing surface having similar annular size and shape so as to apply directly to said boss and only indirectly to said flange via said boss the compression forces which during use will be imposed on said implant fixture.

2. A combination according to claim 1 in which an aperture is provided through gum tissue overlying said jawbone to expose said implant fixture including said flange, and said restoration component means includes a trans-tissue section extending supragingivally from said bearing surface.

3. A combination according to claim 1 in which said implantation body has a length approximately 4 mm to 6 mm, for use in a molar jawbone of shallow depth.

4. A combination according to claim 1 in which a countersink is provided in said surface of said jawbone around said opening to receive said flange.

5. A combination according to claim 4 in which the depth of said countersink is greater than the thickness of said flange, the gingival surface of said flange being recessed below said surface of said jawbone, to encourage growth of bone over said flange.

6. A dental implant fixture having an elongated substantially cylindrical implantation body for implantation in a bore made in the jawbone of a patient to receive said implant, said implant fixture when so implanted having a gingival end located in the opening into said bore, an annular flange on said body extending therefrom laterally around said gingival end for overlying the surface of said jawbone around said opening when said fixture is so implanted, and a round boss having substantially the same diameter as said implantation body extending supragingivally from said flange coaxial with said body.

7. A dental implant according to claim 6 having a receiving bore in said implantation body opening centrally through said boss.

8. In combination, a dental implant fixture having an elongated substantially cylindrical implantation body of a first diameter for implantation in a bore having a similar diameter made in the jawbone of a patient to receive said implant fixture, said implant fixture when so implanted having a gingival end located in the opening into said bore, an annular flange on said body extending therefrom laterally around said gingival end to a second larger diameter for overlying the surface of said jawbone around said opening when said fixture is so implanted, and an annular boss extending supragingivally from said flange, said boss having substantially the same outer diameter as and being concentric with said implantation body, a receiving bore in said implantation body opening centrally through said boss, and prosthodontic restoration component means which is tubular in shape having at one end a first transverse annular surface providing a bearing surface for contacting said implant fixture at said gingival end, means for engaging in said receiving bore to join said restoration component to said implant fixture, the outer diameter of said bearing surface being substantially the same as said second larger diameter of said flange and the inner diameter of said bearing surface being substantially the same as said first diameter of said implantation body, and extending axially inward from said bearing surface a circular recess dimensioned loosely to envelop said boss.

* * * * *